US009804132B2

(12) United States Patent
Hoyt

(10) Patent No.: US 9,804,132 B2
(45) Date of Patent: Oct. 31, 2017

(54) LINKAGE ASSEMBLY FOR IN-LINE INSPECTION TOOL

(71) Applicant: Philip M. Hoyt, Murray, UT (US)

(72) Inventor: Philip M. Hoyt, Murray, UT (US)

( * ) Notice: Subject to any disclaimer, the term of this patent is extended or adjusted under 35 U.S.C. 154(b) by 62 days.

(21) Appl. No.: 15/015,596

(22) Filed: Feb. 4, 2016

(65) Prior Publication Data

US 2016/0231279 A1 Aug. 11, 2016

Related U.S. Application Data

(60) Provisional application No. 62/114,454, filed on Feb. 10, 2015.

(51) Int. Cl.
| | |
|---|---|
| *F16L 55/26* | (2006.01) |
| *G01N 29/22* | (2006.01) |
| *G01N 29/24* | (2006.01) |
| *G01N 29/265* | (2006.01) |
| *G01N 27/83* | (2006.01) |

(52) U.S. Cl.
CPC .......... *G01N 29/225* (2013.01); *G01N 27/83* (2013.01); *G01N 29/2412* (2013.01); *G01N 29/265* (2013.01)

(58) Field of Classification Search
CPC .................................................... F16L 55/26
See application file for complete search history.

(56) References Cited

U.S. PATENT DOCUMENTS

| | | |
|---|---|---|
| 3,786,684 A | 1/1974 | Wiers et al. |
| 3,949,292 A | 4/1976 | Beaver et al. |
| 3,967,194 A | 6/1976 | Beaver et al. |
| 4,006,359 A | 2/1977 | Sullins et al. |
| 4,105,972 A | 8/1978 | Smith |
| 4,447,777 A | 5/1984 | Sharp et al. |
| 4,769,598 A | 9/1988 | Krieg et al. |
| 4,835,876 A | 6/1989 | Petermann et al. |
| 4,852,391 A | 8/1989 | Ruch et al. |
| 4,953,412 A | 9/1990 | Rosenberg et al. |
| 4,964,059 A | 10/1990 | Sugaya et al. |
| 5,293,117 A | 3/1994 | Hwang |
| 5,309,844 A | 5/1994 | Zollinger |
| 5,565,633 A | 10/1996 | Wernicke |
| 5,864,232 A | 1/1999 | Laursen |
| 6,023,986 A | 2/2000 | Smith et al. |
| 6,087,830 A | 7/2000 | Brandley et al. |
| 6,232,773 B1 | 5/2001 | Jacobs et al. |
| 6,427,602 B1 | 8/2002 | Hovis et al. |

(Continued)

*Primary Examiner* — Robert R Raevis
(74) *Attorney, Agent, or Firm* — Pate Baird, PLLC

(57) ABSTRACT

An in-line pipeline inspection tool includes a plurality of sensors assemblies distributed about a central body. Each sensor assembly includes a sensor body coupled at the ends thereof to the central body by first and second linkage assemblies. The linkage assemblies include first and second links, the first link coupled by a first pivot to the central body and by a second pivot to the second link. The second link is coupled to the sensor body by a third pivot. As the tool is moved in one direction, the sensor body is urged away from the first linkage assembly, which engages a block that prevents further rotation of about one of the pivots. As the tool is moved in another direction, the block disengages, thereby permitting rotation about all three pivots. The second linkage assembly functions in an identical fashion.

19 Claims, 15 Drawing Sheets

(56) References Cited

U.S. PATENT DOCUMENTS

| | | | |
|---|---|---|---|
| 6,450,104 B1 | 9/2002 | Grant et al. | |
| 6,538,431 B2 | 3/2003 | Couchman et al. | |
| 6,640,655 B1 * | 11/2003 | Manzak | F17D 5/00 73/865.8 |
| 6,847,207 B1 | 1/2005 | Veach et al. | |
| 6,910,533 B2 | 6/2005 | Guerrero | |
| 7,256,576 B2 | 8/2007 | Mandziuk et al. | |
| 7,334,642 B2 | 2/2008 | Doering et al. | |
| 7,548,059 B2 | 6/2009 | Thompson et al. | |
| 7,798,023 B1 * | 9/2010 | Hoyt | F16L 55/28 73/865.8 |
| 2001/0017541 A1 | 8/2001 | Kwun et al. | |
| 2003/0089267 A1 | 5/2003 | Ghorbel et al. | |
| 2006/0248966 A1 | 11/2006 | Houldey et al. | |

* cited by examiner

LINKAGE ASSEMBLY FOR IN-LINE INSPECTION TOOL

RELATED APPLICATION

This application claims the benefit of U.S. Provisional Application 62/114,454 Filed Feb. 10, 2015, which is hereby incorporated by reference.

BACKGROUND

1. Field of the Invention

This invention relates to pipeline inspection tools, and more particularly to apparatus and methods for linking sensors or inspection assemblies in an in-line inspection tool.

2. Background Art

Pipeline inspection tools, commonly called "smart pigs," have been used for the last half-century or more to determine the condition of pipeline by examining it from the interior of the pipeline. Such tools use a variety of inspection technologies including mechanical geometric examination, ultrasonic inspection of several types (UT), eddy current examination, magnetic flux leakage technology (MFL), electromagnetic acoustic transducer (EMAT) technology and others. These tools use instrumentation of diverse types to introduce a measurement field and sensors to collect data from the field. The base instrumentation and the sensors are mounted to an inspection tool and contact the inside of the pipe wall either directly by the instrumentation itself or indirectly through supporting or coupling arrangements. This contact must be compliant to allow inspection devices or their supporting structure to connect with the wall even when the inside shape of the pipeline may change due to intruding features or pipe wall damage. That contact may prevent the inspection tool from moving in a reverse direction without damaging the inspection devices or other parts of the inspection tool. All known inspection technologies require this contact or coupling and conventional inspection tools are generally incapable of moving in a reverse direction without damage.

The apparatus disclosed herein provides an improved pipeline inspection tool.

BRIEF SUMMARY OF THE INVENTION

In one aspect of the invention, a sensor system includes a central body defining a central axis. A plurality of sensor assemblies are mounted to the central body and distributed circumferentially around the central axis. Each sensor assembly of the plurality of sensor assemblies includes a sensor body having at least one sensor mounted thereto and first and second linkage assemblies mounted to the sensor body having the at least one sensor positioned between the first and second linkage assemblies.

Each linkage assembly of the first and second linkage assemblies includes (a) a first link, (b) a second link, (c) a first pivot coupling the first link to the central body, (d) a second pivot coupling the second link to the first link, (e) a third pivot coupling the second link to the sensor body, and (f) a block positioned to prevent rotation of at least one of the first and second links about one of the first, second, and third pivots in response to urging of the sensor body away from the each linkage assembly.

In some embodiments, the block is positioned to permit rotation of the at least one of the first and second links about the one of the first, second and third pivots in response to urging of the sensor body toward the each linkage assembly.

In some embodiments, the block is positioned to restrict rotation of the first link about the first pivot in response to urging of the sensor body away from the each linkage assembly.

The central body defines a radial direction perpendicular to the central axis and radiating outward from the central axis. The block is positioned to restrict rotation of the first link such that the second pivot is rotatable inwardly from the first pivot no more than between 20 and 45 degrees from the radial direction, preferably no more than between 25 and 35 degrees from the radial direction, and more preferably no more than between 30 and 32 degrees from the radial direction. In particular, experiments conducted by the inventor have shown that permitting rotation of no more than between 30 and 32 degrees from the radial direction provides particularly good operation.

In some embodiments, the block is positioned to permit rotation of the first link outwardly from the first pivot by at least 60 degrees from the radial direction, preferably at least 90 degrees outwardly form the radial direction. In some embodiments, the block is mounted to the central body. The first pivot may rotatably secure the first link to the block. In some embodiments, the block defines a sloped surface facing outwardly and defining an angle of between 25 and 35 degrees with respect to the radial direction.

In some embodiments, the block is secured to the first link. For example, the block may be monolithically formed with the first link.

In some embodiments, the first and second linkage assemblies are sized and positioned relative to one another such that the first, second, and third pivots of the first and second linkage assemblies are not permitted to move such that an inward facing angle between the first and third pivots about the second pivot exceeds 180 degrees.

The at least one sensor may be a magnetic flux leakage (MFL) sensor, ultrasonic sensor, or an electromagnetic acoustic transducer (EMAT).

In some embodiments, the first, second, and third pivots permit rotation exclusively in a radial plane, the radial plane being parallel to the central axis and radiating outwardly from the central axis.

In another aspect of the invention, a method for inspecting a pipeline includes providing a sensor system including (A) a central body defining a central axis and (B) a plurality of sensor assemblies mounted to the central body and distributed circumferentially around the central axis, each sensor assembly of the plurality of sensor assemblies including (i) a sensor body having at least one sensor mounted thereto and (ii) first and second linkage assemblies mounted to the sensor body having the at least one sensor positioned between the first and second linkage assemblies, each linkage assembly of the first and second linkage assemblies including (a) a first link, (b) a second link, (c) a first pivot coupling the first link to the central body, (d) a second pivot coupling the second link to the first link, and (e) a third pivot coupling the second link to the sensor body, (f) a block positioned to prevent rotation about one of the first, second, and third pivots in response to urging of the sensor body away from the each linkage assembly.

The method further includes inserting the sensor system in the pipeline such that the sensor bodies of the plurality of sensor assemblies engage an inner wall of the pipeline. The sensor system is urged through the pipeline in a first direction such that the inner wall urges the sensor bodies of the plurality of sensor assemblies toward the first linkage assemblies thereby causing the blocks of the first linkage assemblies to prevent rotation about the one of the first, second and third pivots of the first linkage assemblies.

The sensor system is then urged through the pipeline in a second direction opposite to the first direction such that the inner wall urges the sensor bodies of the plurality of sensor assemblies away from the first linkage assemblies thereby causing the blocks of the first linkage assemblies to cease preventing rotation about the one of the first, second and third pivots of the first linkage assemblies.

In some embodiments, causing the blocks of the first linkage assemblies to prevent rotation about one of the first, second, and third pivots of the first linkage assemblies includes urging the first link into engagement with the block.

In some embodiments, causing the blocks of the first linkage assemblies to cease preventing rotation about the one of the first, second and third pivots of the first linkage assemblies comprises urging the first link out of engagement with the block.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
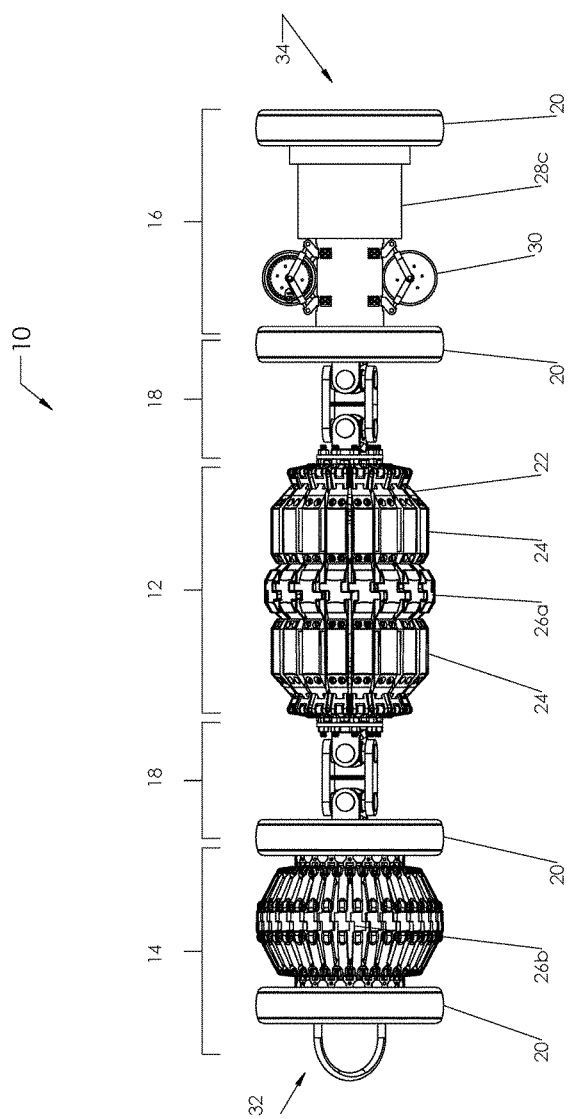
FIG. 1 is an elevation view of one embodiment of an MFL ILI tool in accordance with an embodiment of the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

A typical inspection system and perhaps the most common such system is magnetic flux leakage (MFL). It must be remembered that most inspection systems are subject to the same limitations on reversibility and that a solution to these limitations will apply to all inspection systems. By way of illustration this discussion is presented as it applies to an MFL system. In such a system, flaws in ferromagnetic pipe can be detected by the perturbations they cause in a magnetic field applied to the wall of a pipeline. An MFL inspection tool carries magnets that serve as the basic instruments to induce the magnetic field and sensors that monitor the magnetic flux density as it changes due to the presence of pipeline flaws.

To collect useful data, the sensors carried by an MFL tool, or for that matter any in-line inspection tool, must closely track the interior of the pipe being inspected. However, the interior surfaces of pipes are not uniform and the magnets and sensors must move relative to the central parts of the inspection tool as the tool passes pipe sections with varying interior surfaces. For that reason, the mechanisms connecting the sensors or inspection assemblies to the rest of the in-line inspection tool must accommodate relative movement.

Ever since the mid-1960s when MFL in-line inspection tools were first used for the inspection of pipelines, it has been desirable to insert a tool at a given point in the pipeline, propel it part way through the pipeline and return it to the point of insertion for removal. However, that movement generally has not been possible. The earliest MFL tools used ferromagnetic brushes to couple the magnetic field to the pipe wall. These brushes fold backward somewhat to maintain solid contact between the in-line inspection tool and the pipe wall. Because of that contact angle, they tend to jam against the pipe wall and resist any backward force trying to return the tool to the point of insertion.

In tools with linkages supporting an inspection assembly, the same problem exists. When a tool is reversed, friction and magnetic coupling between the inspection assemblies and the pipe wall jam inspection tools against the front linkages. In the forward direction, these linkages tend to fold inward toward the body of the in-line inspection tool, but in the reverse direction they are forced outward against the pipe wall instead of inward and they jam. Pipelines that necessitate reversal of the inspection tool were classed as being impossible to inspect (termed "unpiggable") because inspection tools could not be inserted, reversed and retrieved.

In one known linkage configuration for non-reversible ILI tools, a single linkage connects an inspection assembly to the central part of the ILI tool at the front of the magnetic assembly. A parallel identical linkage connects the assembly to a similar base on the central part of the ILI tool at the rear of the magnetic assembly. The magnetic assembly is free to move with one degree of freedom in its radial plane. That movement is a translation as the two supporting linkages rotate parallel to one another and the inspection assembly translates without rotation toward the center of the ILI tool. The face of the inspection assembly parallel to the pipe wall remains parallel to the pipe wall. The ILI tool is free to move forward only. Movement of the ILI tool in reverse is prevented because friction forces oppose the movement and force the linkages into compression, the tool jams against the pipe wall and the linkages do not accommodate reverse movement.

Another design is a mechanism that simply does not include a rear linkage, relying on a connection at the front of the assembly. These mechanisms cannot control the position of the back end of the assembly and that end wanders sideways during any attempted reverse movement, jamming inspection assemblies against the pipe wall and against each other. Yet another design uses a rear link mounted in a slot or a slide, permitting the assembly to move radially relative to the rest of the in-line inspection tool. However, the motion of this design can be significantly hampered when debris fills the slot or slide during inspection. Moreover, attempted reverse movement collapses the slide in a direction opposite to the attempted movement and the linkages again jam.

In another known linkage configuration for non-reversible ILI tools, a single linkage connects an inspection assembly to the central part of the ILI tool at the front of the magnetic assembly and a two-part linkage connects the rear. This introduces an additional degree of freedom, allowing the inspection assembly to rotate as well as translate in the radial plane of the assembly. The movement may be visualized as a translation along the curvilinear path controlled by the rotation of the front linkage and a rotation of the assembly that is allowed by the combination of movements of the rear linkages. These two degrees of freedom allow the inspection assembly to negotiate many pipeline features without losing contact with the pipe wall. However, movement of the ILI tool in reverse is prevented because friction forces oppose the movement and force the front linkage into compression just as discussed in the parallelogram arrangement. The tool jams against the pipe wall and the linkages do not accommodate reverse movement.

In all of the linkage-supported examples given, resistance to reverse movement is especially pronounced and, in fact, is impossible without damaging the ILI tool itself in the presence of any intrusion that presents a surface that is oblique or perpendicular to the surface to the inspection assembly. Such intrusions may include welds, dents, damaged pipe wall, mechanical joints and other local pipeline features.

Most of the foregoing linkage designs prevent rotation of inspection assemblies in the radial plane, allow inspection assemblies to wander away from their designated track, introduce attributes that cause the inspection assemblies to lift away from the pipe or succumb to debris. They all prevent in-line inspection tools from reversing direction.

What is still needed is a mechanism for connecting inspection assemblies to an in-line inspection tool with linkages that allow direction of travel of the tool to be reversed and to still conform to the pipe wall surface. This new mechanism must be reversible, repeatedly permit necessary relative movements moving forward or in reverse, provide precise control over those movements moving forward or in reverse and still pass intrusions easily while moving forward or in reverse.

In view of the foregoing, in accordance with the invention as embodied and broadly described herein, a method and apparatus are disclosed in one embodiment of the present invention as including a tool for the inspection of pipeline from the interior of the line, or an in-line inspection (ILI) tool, comprising sections spaced around the circumference of the ILI tool that carry inspection elements mounted to a central tool body that supports the inspection elements and carries them through the pipeline during inspection. These sections are separated and mounted on supports or linkages that hold them near or against the interior of the pipe wall. The linkages collapse toward the pipe center to allow the inspection tool to fit inside the pipeline and to pass through pipe with different wall thicknesses, bends, changes in diameter and other general pipeline features, or with intrusions such as circumferential welds, dents, damaged pipe wall, mechanical joints and other local pipeline features.

The sections that carry inspection elements (i.e., inspection assemblies) are restricted by the linkages to move within a single radial plane (i.e., a plane containing the central axis of the in-line inspection tool and a radial vector through the center of the inspection assembly). The linkages attach the inspection assemblies to the body of the tool and allow them to move in translation toward or away from the tool body while also allowing them to rotate in the radial plane of the pipeline. These two degrees of freedom (translation and rotation) provide the movement necessary to allow inspection elements to move inward as they encounter obstacles and also to rotate over such obstacles in order to hinder liftoff. Moreover, the tool comprises an additional degree of freedom that would ordinarily introduce instability or lack of control. Such lack of control would tend to allow or even force inspection elements to lose contact with the interior pipe wall, which in turn would impair the inspection. In some embodiments, the additional degree of freedom is controlled by the further addition of blocks that remove the instability and allow the tool to move in either a forward or reverse direction with full freedom of movement without constriction.

In a configuration where the inspection elements are magnetic flux leakage (MFL) magnets and sensors, magnetic assemblies comprising the magnets and sensors are mounted against the interior pipe wall and they travel in contact with the wall. Linkages in accordance with the invention support both translational and rotational movement of the magnetic assemblies within their radial planes. These two degrees of freedom permit the MFL ILI tool to pass through the pipeline with an orientation suitable for inspection. The linkages and ancillary supporting elements also hold the magnetic assemblies against the interior surface of the pipeline being inspected despite gravitational forces, magnetic forces and the like that may depress inspection assemblies toward the central axis of the ILI tool. In some embodiments, the linkages according to an embodiment of the invention may include two sub-linkages at both the front and the rear of a magnetic assembly. These four sub-linkages provide excess movement beyond the two degrees of freedom described, but blocks attached to the central body of the ILI tool restrict movement of the magnetic assembly to only the required two degrees of freedom. By the inclusion of excess sub-linkages and restricting blocks, this embodiment allows control of the required degrees of freedom to shift from one end of the magnetic assembly to the other as the ILI tool may move from forward to reverse, thus precluding the existence of forces that would otherwise jam the ILI tool as its movement changes from forward to reverse.

Moving in the forward direction of the inspection tool, forward motion holds the inside section of the forward linkage against a block that constricts its movement to rotation of its outside sub-linkage and allows only one degree of freedom for the forward linkage. Simultaneously, the rear linkage is forced away from its counterpart block and both sections of the rear linkage are free to rotate while still attached to the inspection assembly, providing a second degree of freedom for the inspection assembly. Excess movement in the form of additional degrees of freedom is precluded by constraint of the forward linkage against its block to provide only one degree of freedom there. When movement of the inspection tool is reversed, rearward movement holds the inside section of the rear linkage against its counterpart block, the forward linkage moves toward the front of the tool and both of its sections are free to rotate. The inspection assembly again has two degrees of freedom without excess movement. Either forward or rearward movement may be accommodated and the inspection tool is reversible.

In selected embodiments, the leading linkage includes two sub-linkages and three pivots and a trailing linkage similarly comprises two sub-linkages and three similar or identical pivots. As the inspection tool moves forward, the leading linkage as constrained by the block provides one degree of freedom to the inspection assembly and the trailing linkage adds a second degree of freedom and the assembly, thus having two independent degrees of freedom, accommodates both translation and rotation to allow it to follow interior contours of the pipeline wall. The trailing linkage moves away from a second block adjacent to or part of the trailing section connected to the body of the inspection tool and the second block is not functional.

When the inspection tool moves rearward, roles of the linkages are reversed and the entire tool is reversible. It should be noted that the embodiment disclosed herein does not depend on the location of its various elements. For instance, the blocks may be located on the inspection assembly or on the linkages themselves rather than on the body of the tool and may function the same way when so located. By providing comparable movement of the inspection tool in the forward or rearward directions of the tool without reconfiguring the tool, the inspection tool is capable of reverse movement without being forced against the pipe wall. By strictly limiting movement of the inspection assemblies to movements within their radial planes and controlling the movement therein, leading and trailing linkages control the circumferential spacing between inspection assemblies more precisely. This in turn may produce better data on the pipeline being inspected. By supporting rotation of inspection assemblies within the radial plane, leading and trailing linkages may provide close tracking of the interior surfaces of the pipeline being inspected. Moreover, by relying exclusively on pivots and pivoting and not slots and sliding, leading and trailing linkages in accordance with the present invention function precisely and repeatably, even in very dirty environments.

Although the invention is described herein in the context of a magnetic-flux-leakage in-line inspection tool, the invention may be used in conjunction with other sensing technologies. For example, the invention may be applied to in-line inspection tools utilizing ultrasonic inspection (UT), eddy current inspection, electro-magnetic acoustic transducer (EMAT) inspection, video or other optical inspection, acoustic or acoustic interferometry inspection, various electronic or electronic interferometry inspection, and the like.

The drawings as referred to above together with the following description and claims illustrate the composition and function of a pipeline In-Line Inspection (ILI) tool according to an embodiment of the invention. The drawings illustrate typical embodiments of an MFL implementation of the invention but do not limit its scope; other MFL tools or tools utilizing other inspection technologies are equally represented. The drawings show components of the invention as they function together and illustrate the form and function of an ILI tool according to an embodiment of the invention. Numbers on the drawings refer to specific components of the tool and are common for each particular component throughout the drawings without regard to the view or other components shown.

In operation, an MFL ILI tool moves along the interior axis of a pipeline. Components of the invention may be seen in FIGS. 1 through 15 as referenced above. Flexible components 20 (disks) of the ILI tool 10 may seal against the interior wall of the pipeline so that the ILI tool may move with the fluid moving through the pipeline or the ILI tool may be propelled by other means such as cable pulling mechanisms or the like (not shown). Magnets 24 as shown in FIG. 1 mounted to the tool induce magnetic flux into the pipeline at a flux density strong enough to saturate the pipe wall. In undamaged sections of pipe, there is a strong uniform magnetic field in the pipe wall and a weaker uniform magnetic field just inside the pipe adjacent to the pipe wall. This weaker field is termed the leakage field. Anomalies such as corrosion or physical damage to the pipe that produce loss of material in the pipe wall cause perturbations in the magnetic field, both within the pipe wall and in the leakage field. Sensors 26*a* also mounted to the ILI tool 10 monitor the leakage field and sense the changes caused by pipe wall damage. Data from the full leakage field is stored onboard the ILI tool 10, typically in canisters 28 some of which may be obscured to view in FIG. 1 by other components of the ILI tool 10. The perturbations to the leakage field are correlated to the pipe wall damage and the damage is characterized through analytical techniques. Damage that is severe enough to affect integrity of the pipeline is identified, located, characterized and reported to the pipeline operator so that corrective measures may be taken. ILI tools using other inspection technologies similarly introduce an inspection field into the pipe wall and monitor the field to find and evaluate pipe wall damage. ILI tools use support mountings that hold inspecting elements in position and that are shown in detail in other figures. Mountings for inspection technologies other than MFL are fully analogous to the mountings disclosed herein and are therefore other applications for the invention.

An MFL ILI tool 10 with a front end 32 and a reverse end 34 according to an embodiment of the invention is shown in FIG. 1 where a lead section 14 of the tool comprises drive mechanisms 20 that propel the tool through a pipeline as a pressure differential is produced across them by pumps or gravity forcing a fluid (liquid or gas) to flow through the pipeline. The lead section 14 may further comprise functional components of the tool interior to canisters 28b (obscured by inspection devices 26b in FIG. 1) such as embedded computers, data processors, inertial navigation or mapping components, power supplies, data storage components and the like as well as components external to the canister such as inspection devices 26b. In place of MFL devices, external inspection devices 26b may include geometry measurement devices, devices to determine the location of anomalies as to their position on the inside or outside of the pipe wall, devices to measure cathodic protection currents, distance measurement devices and the like.

Other sections of the ILI tool 10 comprise a magnetic section 12 with magnetic assemblies 22 which further comprise magnets 24 and sensors 26a. The magnetic assemblies 22 are flexibly connected to center parts of the ILI tool 10 by linkages 50, 52 that allow the magnetic assemblies 22 to collapse and expand toward and away from central portions of the ILI tool 10.

An ILI tool 10 may comprise other sections 16 with additional canisters 28c comprising embedded computers, data processors, inertial navigation or mapping components, power supplies, data storage components and the like on their interior and may further comprise other inspection devices (26, 30) such as geometry measurement devices, devices to determine the location of anomalies as to their position on the inside or outside of the pipe wall, devices to measure cathodic protection currents, distance measurement devices and the like on their exterior. Sections of the tool are connected by couplers 18 which may flex to accommodate passage around bends in the pipeline.

An ILI tool 10 may comprise one or more of the sections shown in FIG. 1. An ILI tool according to an embodiment of the invention may move forward toward the front of the tool 32 or in reverse toward the back of the tool 34 without conflict and without seizing against the pipe wall. Accordingly, the last section 16 may comprise components much the same as those of the leading section 14, e.g. in a mirrored configuration, so that the tool may be propelled in a reverse direction as the fluid (liquid or gas) may be pumped in a reverse direction. Furthermore, in some applications the ILI tool according to an embodiment of the invention may be propelled in one direction by a pumped fluid and propelled in the opposite direction by mechanical means such as a cable, wire, wire rope, chain, rope or the like; may be propelled in one direction by mechanical means and propelled in the opposite direction by fluid flow; or any combination of any such means or similar means as is obvious to one familiar with such means of propulsion.

Figure 2:
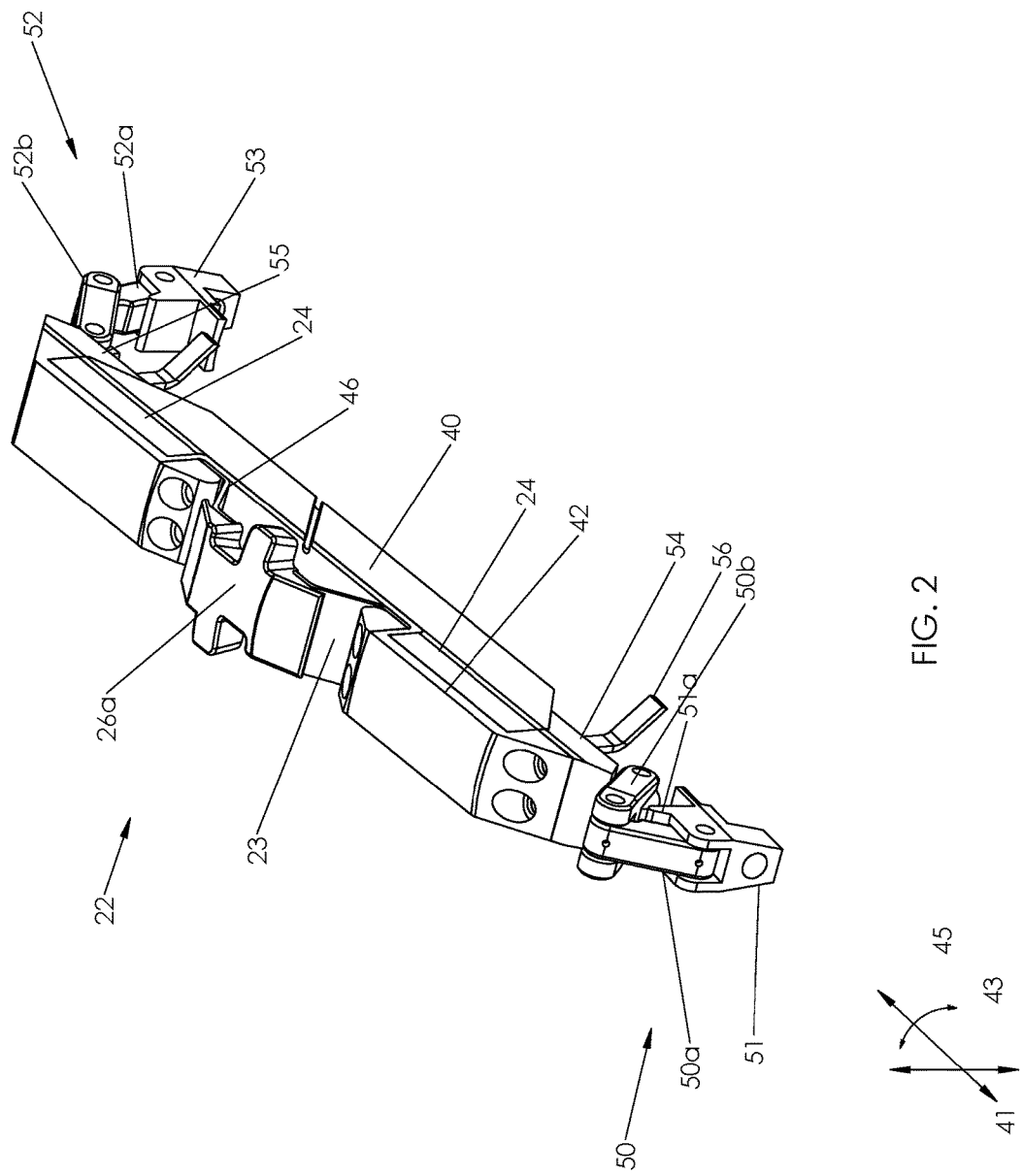
FIG. 2 is a perspective view of one embodiment of an inspection assembly in accordance with an embodiment of the present invention.

As shown in FIG. 2, an MFL magnetic assembly 22 according to an embodiment of the invention may be comprised of an armature 40, magnets 24, wear plates 42 which serve to hold magnets in place and to buffer wear between the magnets 24 and the wall of the pipeline, sensors 26a, and linkage assemblies 50, 52 that connect blocks 54, 55 fastened to the armature 40 to linkage blocks 51, 53 fastened to central components of the ILI tool. Movement of magnetic assemblies 22 is constrained by linkage assemblies 50, 52 to a single radial plane, a plane containing the axis 41 of the ILI tool and a radial vector 43 from the axis 41 of the ILI tool 10 in the center plane of the magnetic assembly 22. A full set of magnetic assemblies comprises individual magnetic assemblies 22 spaced uniformly around the circumference 45 of the ILI tool 10.

As illustrated in FIG. 2, the invention comprises two linkages 50 and 52 each of which is comprised of two sub-linkages 50a, 50b and 52a, 52b respectively, thus providing two linkages at the front and two linkages at the rear of magnetic assembly 22. Sub-linkage 50a is attached to a block 51 which comprises part of the central body of the ILI tool 10 near the front of the magnetic assembly 22 and sub-linkage 52a is secured to a block 53 which comprises part of the central body of the ILI tool 10 near the rear of the magnetic assembly 22. The distance between mount 51 at the front of the magnetic assembly 22 and mount 53 at the rear of the magnetic assembly 22 is fixed.

Figure 3:
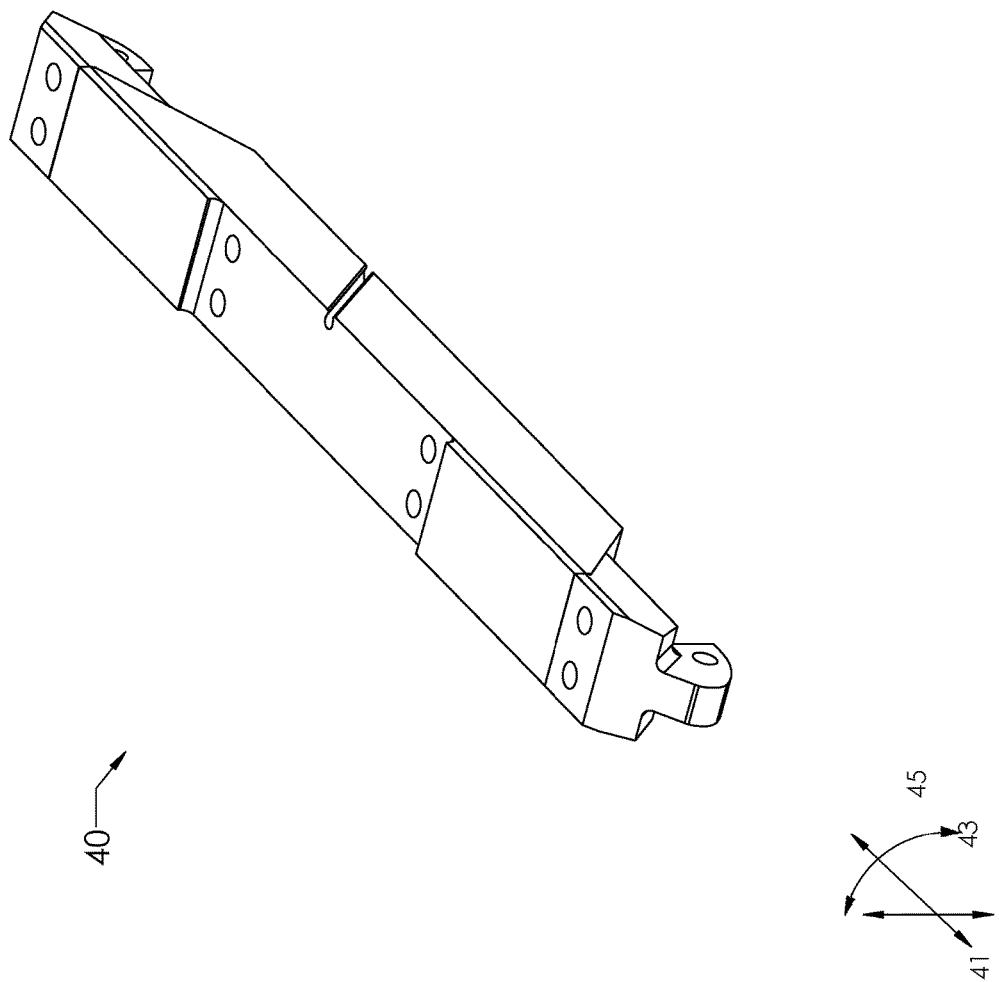
FIG. 3 is a perspective view of an armature of an MFL inspection assembly with its mount and attachments for linkages in accordance with an embodiment of the present invention.

FIG. 3 shows an individual armature 40 that magnetically connects magnets 24 (shown in FIGS. 1 and 2) to complete a magnetic circuit when magnetic assemblies 22 (also shown in FIGS. 1 and 2) are in contact with the pipe wall. In addition to serving as part of the magnetic circuit, armature 40 comprises the basic supporting structure of magnetic assemblies 22. Linkages 50 and 52 (shown in FIG. 2) are connected to the armature at blocks 54 and 55 (shown in FIG. 2) at respective ends of the armature and consequently control movement of the magnetic assembly 22 according to an embodiment of the invention.

When magnetic assemblies 22 (shown in FIGS. 1 and 2) are positioned in contact with the pipe wall, magnetic force of attraction between magnets 24 and the pipe wall tends to hold magnetic assemblies 22 against the pipe wall and away from central portions of the ILI tool 10. Indeed, even when the ILI tool is out of the pipe, and magnetic assemblies 22 are fully extended, magnetic forces between identical magnets 24 located in adjacent magnetic assemblies 22 tend to repel one another. Since these adjacent magnets 24 are circularly positioned they are inclined relative to one another and the repelling force between them has an outward component. The outward component tends to keep magnet assemblies fully extended. However, that position is an unstable position of high potential energy in the magnetic field. Magnets 24 tend to drop toward the center of the ILI tool 10, a position of lower potential energy. The movement is the same as when a ball in equilibrium in a gravity field resting on top of a larger ball tends to roll away from the position of unstable equilibrium and high potential energy at the top and fall to a position of lower potential energy. Any disturbance in the equilibrium position of a magnetic assembly within the full set of magnetic assemblies 22 may cause the disturbed assembly to drop toward the center of the ILI tool 10. To preclude this movement, levers 56 (shown in FIG. 2), longer than the distance between magnetic assemblies and attached to each magnetic assembly, may extend beyond each individual magnetic assembly and support adjacent magnetic assemblies. Interleaved in this way, levers 56 provide limits to the radial movement of individual magnetic assemblies 22 and keep all magnetic assemblies 22 in extended positions. Levers 56 may be attached to armatures 40 at the front and at the rear of armatures 40 with a pivot that rotates to align levers with magnetic assemblies to provide space for removal of individual magnetic assemblies from the field of all magnetic assemblies for maintenance or the like.

Figure 4:
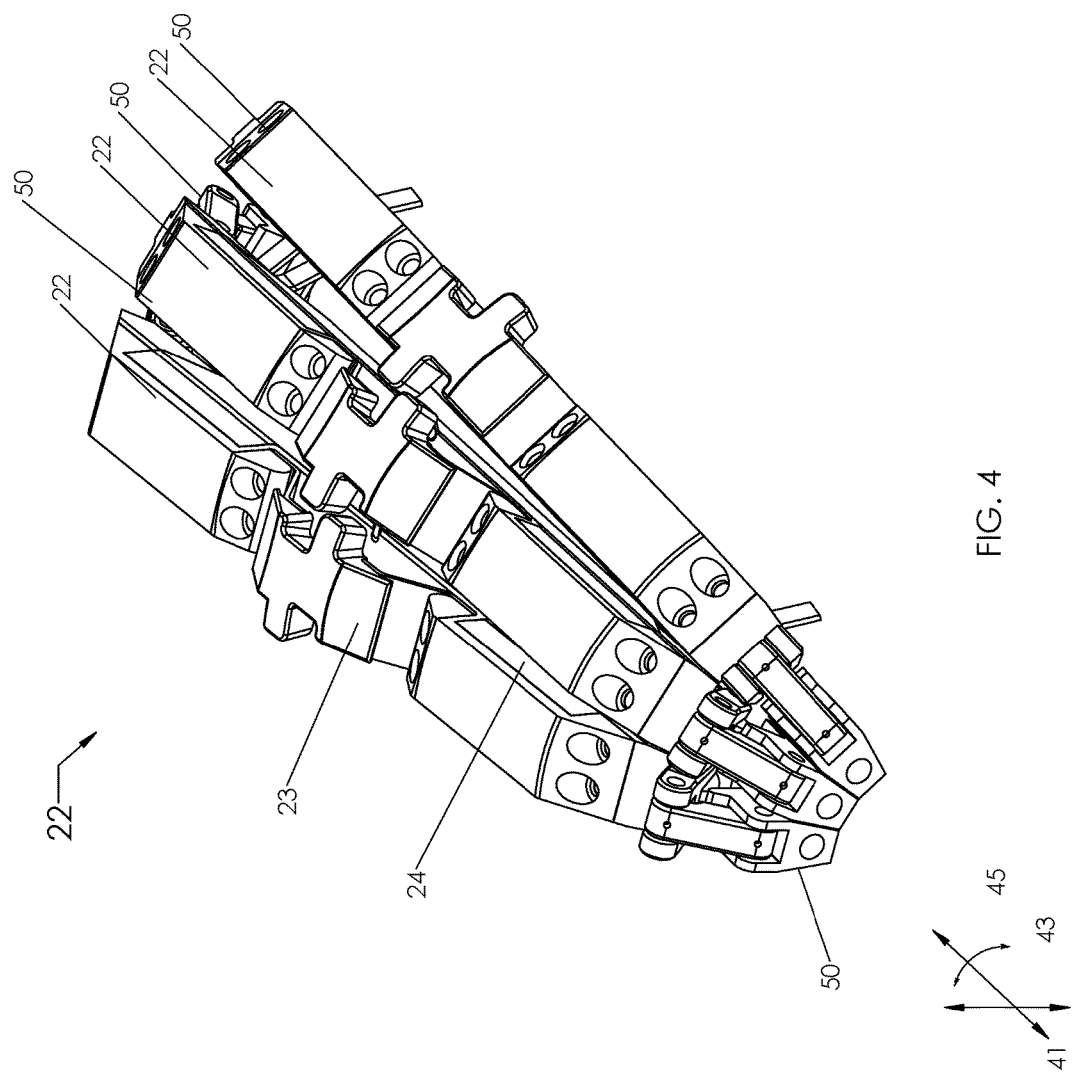
FIG. 4 is a perspective view of a group of magnetic assemblies as they fit around the circumference of an MFL ILI tool in accordance with an embodiment of the present invention.

FIG. 4 shows a group of magnetic assemblies 22 that comprise part of a full circumference of individual magnetic assemblies 22 as they are supported by linkages 50 and 52. Each individual magnetic assembly 22 is free to move in its own radial plane. Each individual magnetic assembly is independent of neighboring magnetic assemblies except as they may be limited by levers 56 as discussed above.

Figure 5:
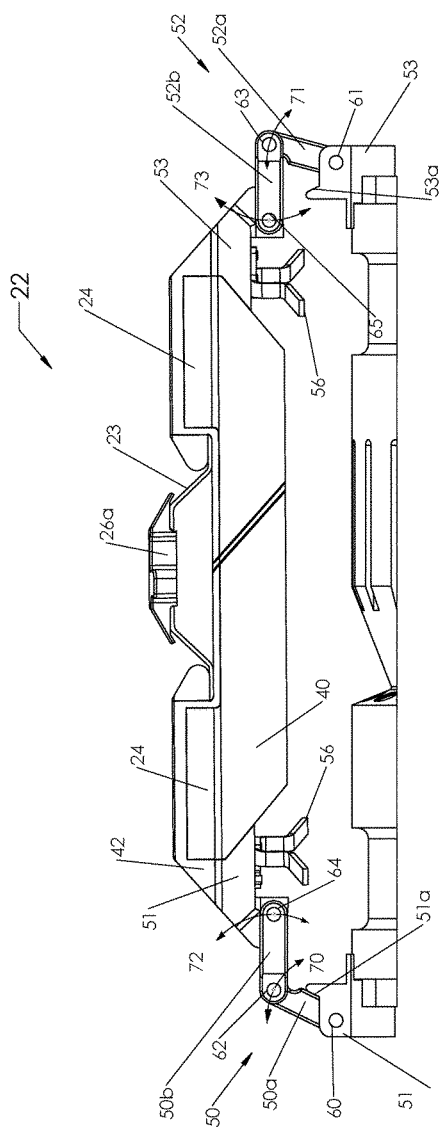
FIG. 5 is an elevation view of one embodiment of an inspection assembly attached to a section of the body of an ILI tool showing elements positioned to accommodate forward movement in accordance with an embodiment of the present invention.

As the ILI tool 10 moves forward to the left, friction holds the magnetic assembly 22 in FIG. 5 against the pipe wall and resists the forward motion. The main body of the ILI tool 10 moves to the left relative to the magnetic section 22 as more fully shown in FIG. 5. A sloping or normal surface 51*a* on block 51 contacts sub-linkage 50*a* and precludes further movement of sub-linkage 50*a* relative to the magnetic assembly 22. The magnetic assembly 22 is then effectively supported at its front by a single linkage 50*b* and the assembly has two degrees of freedom—translation on a curvilinear path 72 defined by rotation of the end of sub-linkage 50*b* about pivot 62 at the now-fixed outer end of sub-linkage 50*a* and rotation of magnetic assembly 22 about pivot 64 at the outer end of sub-linkage 50*b*. Rotations about pivots 61, 63 and 65 may occur and sub-linkages 52*a* and 52*b* (which do not contact block 53) may both rotate. Being free to rotate, sub-linkages 52*a* and 52*b* do not constrict rotation of the magnetic assembly 22. Magnetic assembly 22 may translate with one degree of freedom and rotate with a second degree of freedom. Moreover, magnetic assembly 22 is being pulled by tension in sub-linkage 50*b* in the direction of its movement and no linkages are in compression. Compression of the linkages is undesirable because it forces them into the pipe wall, jams the ILI tool 10 against the pipe wall, and prevents movement.

Two degrees of freedom of the magnetic assembly 22 increase the ability of the assembly to accommodate variations in dimensions of the interior of a pipeline. The ability of the magnetic assembly 22 to translate in its radial plane allows it to move in the radial direction 43 (shown in FIGS. 2, 3 and 4) relative to the main body of the ILI tool 10 and thus to pass by changes in the pipe being inspected. Features such as bends, constrictions, changes in the thickness of the wall of the pipe, circumferential welds, dents, and damaged pipe walls may all be passed. The additional ability to rotate hinders liftoff of the magnetic assembly 22 from the pipe wall and permits magnets 24 to closely track the interior surface of a pipeline in spite of changes in the interior diameter of the pipe. That hinders liftoff from the pipe wall and maintains magnetic saturation in the pipe wall. The ability to rotate also allows sensors 26*a* to closely track the interior surface of a pipeline without liftoff and thereby to accurately measure the magnetic leakage field adjacent to the pipe wall.

While it is beneficial to allow two degrees of freedom for the magnetic assembly 22 in the radial plane as described, provision of more than two degrees of freedom produces unstable or uncontrolled support. There are only three possible degrees of freedom in a plane—two independent translations within the plane and one rotation about an axis normal to the plane. The addition of a third degree of freedom would eliminate control and produce instability. Such lack of control would tend to allow or even force inspection elements to lose contact with the interior pipe wall, which in turn would impair the inspection. The embodiments disclosed herein provides for reverse movement not as an uncontrolled degree of freedom but by providing a center of control of movement of the magnetic assembly 22 that can shift from one end of the magnetic assembly 22 to the other.

According to an embodiment of the invention, the body of the ILI tool 10 forms a base that constrains movements of adjacent components. Block 51 and block 53 are attached to the body of the ILI tool 10 at a fixed distance apart. Linkage 50*a* is connected at pivot 60 to block 51 at one end and to linkage 50*b* at pivot 62 at its other end. Linkage 50*b* is connected to linkage 50*a* at pivot 62 at one end and to the magnetic assembly 22 at pivot 64 at is other end. Block 51 comprises a sloping or normal surface 51*a* that may constrict rotation 70 of linkage 50*a* as described above. Similarly, at the opposite end of the magnetic assembly 22 linkage 52*a* is connected to block 53 at pivot 61 at one end and to linkage 52*b* at pivot 63 at its other end. Linkage 52*b* is connected to linkage 52*a* at pivot 63 at one end and to the magnetic assembly 22 at pivot 65 at its other end. Block 53 comprises a sloping or normal surface 53*a*.

Figure 6:
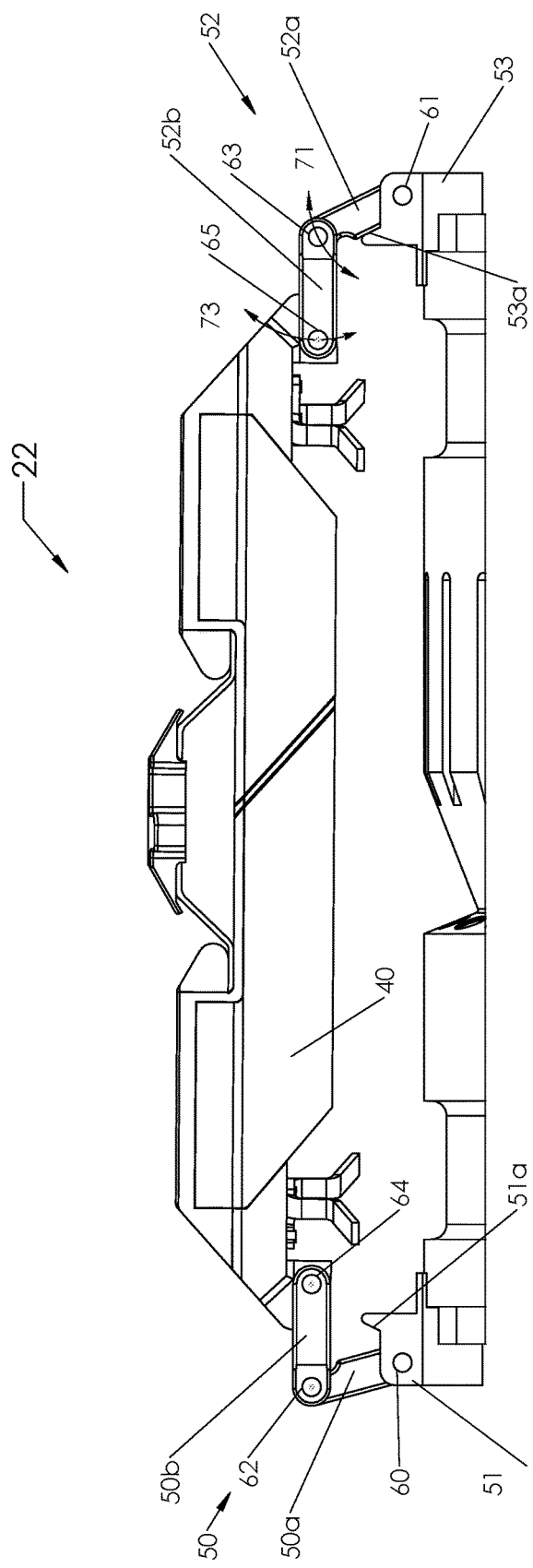
FIG. 6 is an elevation view of one embodiment of an inspection assembly attached to a section of the body of an ILI tool showing elements positioned to accommodate reverse movement in accordance with an embodiment of the present invention.

Reverse movement of the ILI tool 10 as shown in FIG. 6 will force sub-linkage 50*a* away from the sloping or normal surface 51*a* on block 51 and sub-linkages 50*a* and 50*b* will rotate with respect to one another. Simultaneously, block 53 at the rear of magnetic assembly 22 moves toward sub-linkage 52*a* and surface 53*a* contacts sub-linkage 52*a*. Sub-linkage 52*a* becomes fixed relative to surface 53*a* and it is therefore fixed relative to the main body of the ILI tool 10. Movement of the magnetic assembly 22 is now constrained to two degrees of freedom—translation on a curvilinear path 73 defined by rotation of the end of sub-linkage 52*b* about pivot 63 at the now-fixed outer end of sub-linkage 52*a* and rotation of magnetic assembly 22 about pivot 65 at the outer end of sub-linkage 52*b*. Rotations about pivots 60, 62 and 64 may occur and sub-linkages 50*a* and 50*b* (which now do not contact block 51) may both rotate. Being free to rotate, sub-linkages 50*a* and 50*b* do not constrict rotation of the magnetic assembly 22. Magnetic assembly 22 may translate with one degree of freedom and rotate with a second degree of freedom. However, sub-linkage 52*b* is now in tension pulling magnetic assembly 22 in the direction of its movement and no linkages are in compression. Control of the movement of the magnetic assembly 22 has shifted so that a single linkage is pulling the magnetic assembly 22 in the direction of its movement. Again, there is no compression in the linkages that could jam the tool. Regardless of the direction of movement, the ILI tool 10 is not constricted and it is fully reversible.

Figure 7:
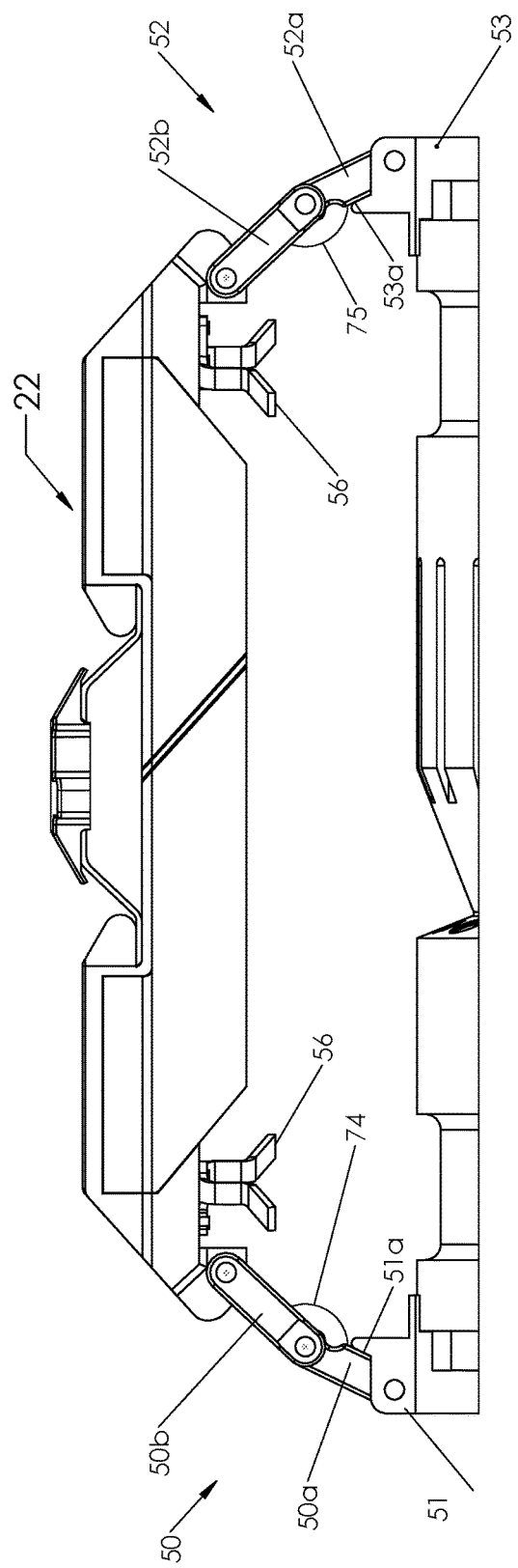
FIG. 7 is an elevation view of one embodiment of a fully extended inspection assembly attached to a section of the body of an ILI tool showing elements that may restrain components of the ILI tool in accordance with an embodiment of the present invention and prevent the tool from entering into adverse configurations.

FIG. 7 shows the magnetic assembly with all of its supporting linkages fully extended. In order to preclude rotations of the linkages that might otherwise cause them to jam against one another and thus hinder movement of the ILI tool 10, the fixed distance between block 51 and block 53, dimensions of the sloping or normal surfaces 51*a* and 53*a*, and the lengths of linkages 50*a*, 50*b*, 52*a* and 52*b* may be such as to maintain the angle 74 between linkages 50*a* and 50*b* and the angle 75 between linkages 52*a* and 52*b* at values no greater than 180 degrees at all times.

Figure 8:
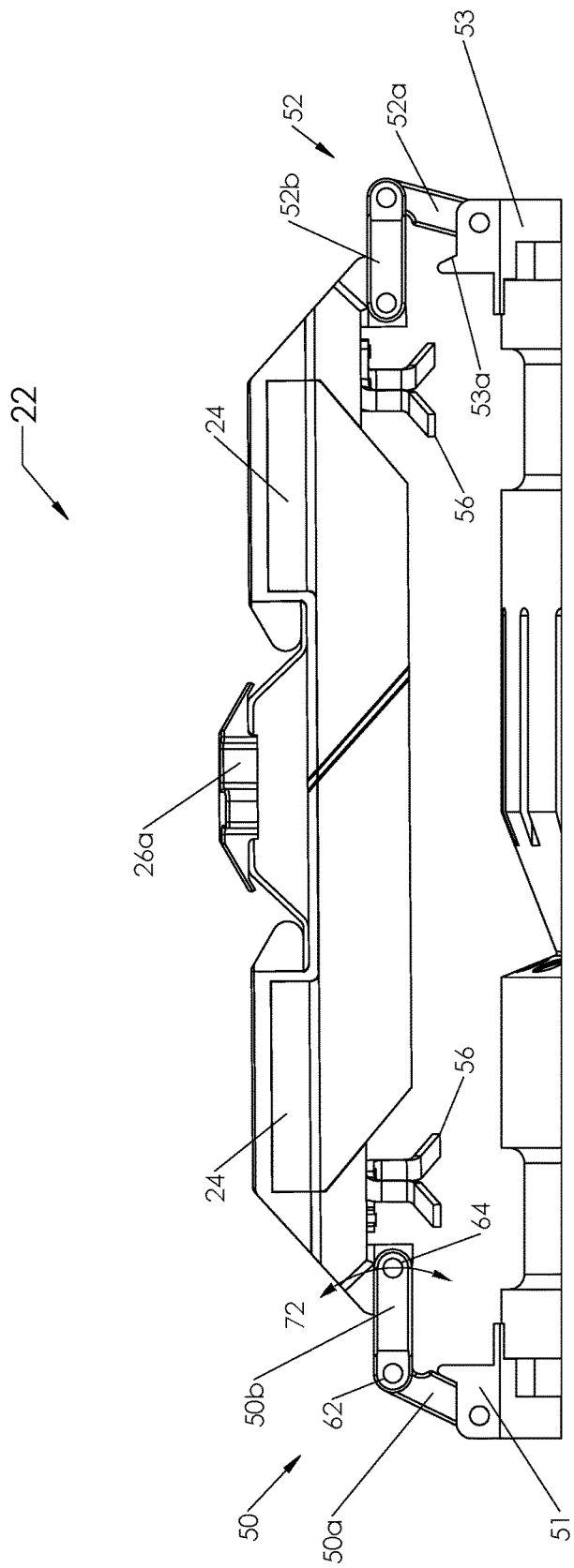
FIG. 8 is an elevation view of one embodiment of an inspection assembly attached to a section of an ILI tool in accordance with an embodiment of the present invention as the ILI tool moves forward inside a pipeline.

FIG. 8 shows the magnetic assembly 22 in a common orientation for inspection of the pipe wall as the ILI tool 10 moves forward to the left. Magnets 24 are positioned in close proximity to the pipe wall so that the pipe wall is magnetically saturated. Sensors 26a are positioned close to the pipe wall to monitor the magnetic flux leakage field and perturbations that may occur in it due to the presence of anomalies in the pipe wall. Friction and magnetic attraction resist the forward motion, holding sub-linkage 50a against the sloping or normal surface 51a of fixed block 51. Sub-linkage 50b is in tension and pulls the magnetic assembly forward as the central body of the ILI tool 10 moves forward. Sub linkages 50b at the front of the magnetic assembly 22 and sub-linkages 52a and 52b at the rear of the assembly constrain the magnetic assembly to movement in its radial plane but allow the assembly to move freely within the plane. The magnetic assembly 22 may translate with one degree of freedom relative to the central body of the ILI tool 10 along the curvilinear path 72, which path may be described as rotation of pivot 64 about pivot 62 which is now fixed to the central body of the ILI tool 10. Freely moving sub-linkages 52a and 52b may allow magnetic assembly 22 to rotate about pivot 64 within the control of the forward pulling force on pivot 64 to provide the second degree of freedom for the assembly. These two degrees of freedom allow the assembly to negotiate dimensional changes within the pipe interior and still hinder liftoff of magnets 24 and sensors 26a.

Figure 9:
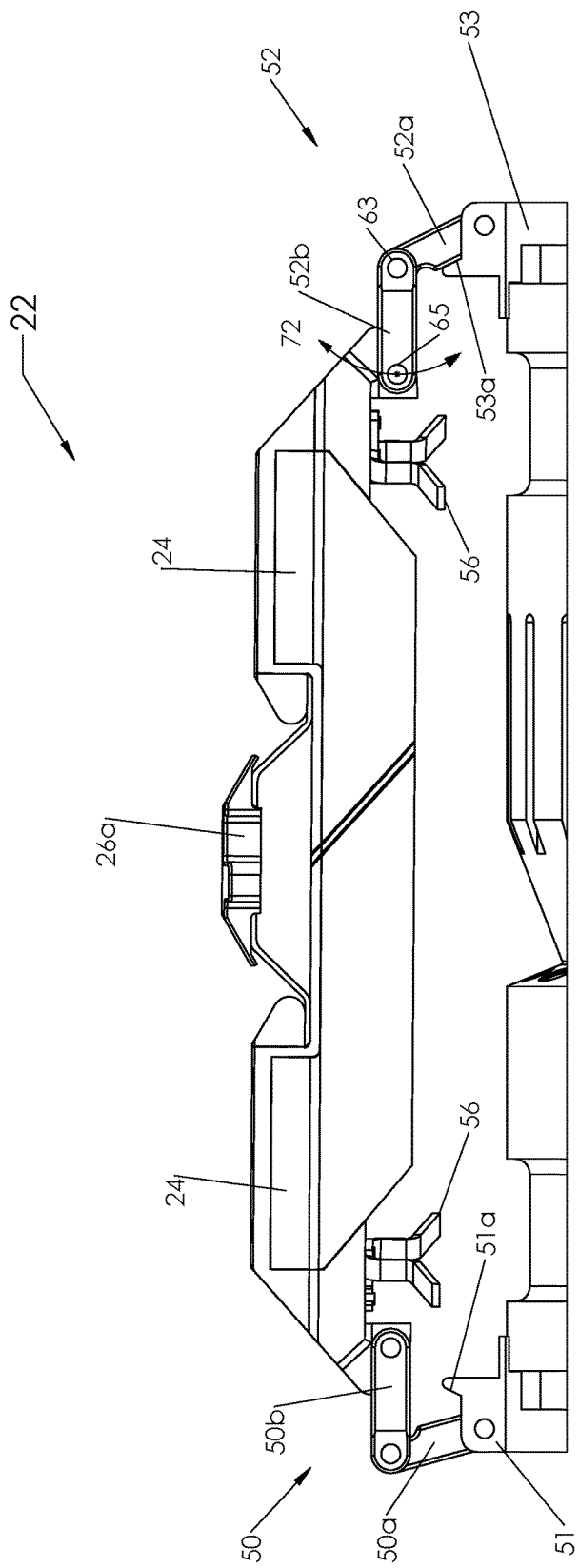
FIG. 9 is an elevation view of one embodiment of an inspection assembly attached to a section of an ILI tool in accordance with an embodiment of the present invention as the ILI tool moves in reverse inside a pipeline.

An event that may cause the ILI tool 10 to reverse direction and to move in reverse to the right as shown in FIG. 9 may be accommodated by an ILI tool 10 as disclosed in this application. The magnetic assembly 22 may be positioned in contact with the pipe wall. Magnets 24 are positioned in close proximity to the pipe wall so that the pipe wall is magnetically saturated. Sensors 26a are positioned close to the pipe wall to monitor the magnetic flux leakage field and perturbations that may occur in it due to the presence of anomalies in the pipe wall. Friction and magnetic attraction resist the reverse motion, holding sub-linkage 52a against the sloping or normal surface 53a of fixed block 53. Sub-linkage 52b is in tension and pulls the magnetic assembly in reverse as the central body of the ILI tool 10 moves in reverse. Sub linkages 52b at the rear of the magnetic assembly 22 and sub-linkages 50a and 50b at the front of the assembly constrain the magnetic assembly to movement in its radial plane but allow the assembly to move freely within the plane. The magnetic assembly 22 may translate with one degree of freedom relative to the central body of the ILI tool 10 along the curvilinear path 73, which path may be described as rotation of pivot 65 about pivot 63 which is now fixed to the central body of the ILI tool 10. Freely moving sub-linkages 50a and 50b may allow magnetic assembly 22 to rotate about pivot 65, which is now within the control of the rearward pulling force on pivot 65 to provide the second degree of freedom for the assembly. These two degrees of freedom again allow the assembly to negotiate dimensional changes within the pipe interior and still hinder liftoff of magnets 24 and sensors 26a. The movement in reverse is exactly parallel to the forward movement described in reference to FIG. 8, but control has now shifted to the rear of magnetic assembly 22 and conflicts in movement that might jam a reverse-moving ILI tool 10 without the embodiments disclosed herein are resolved.

Figure 10:
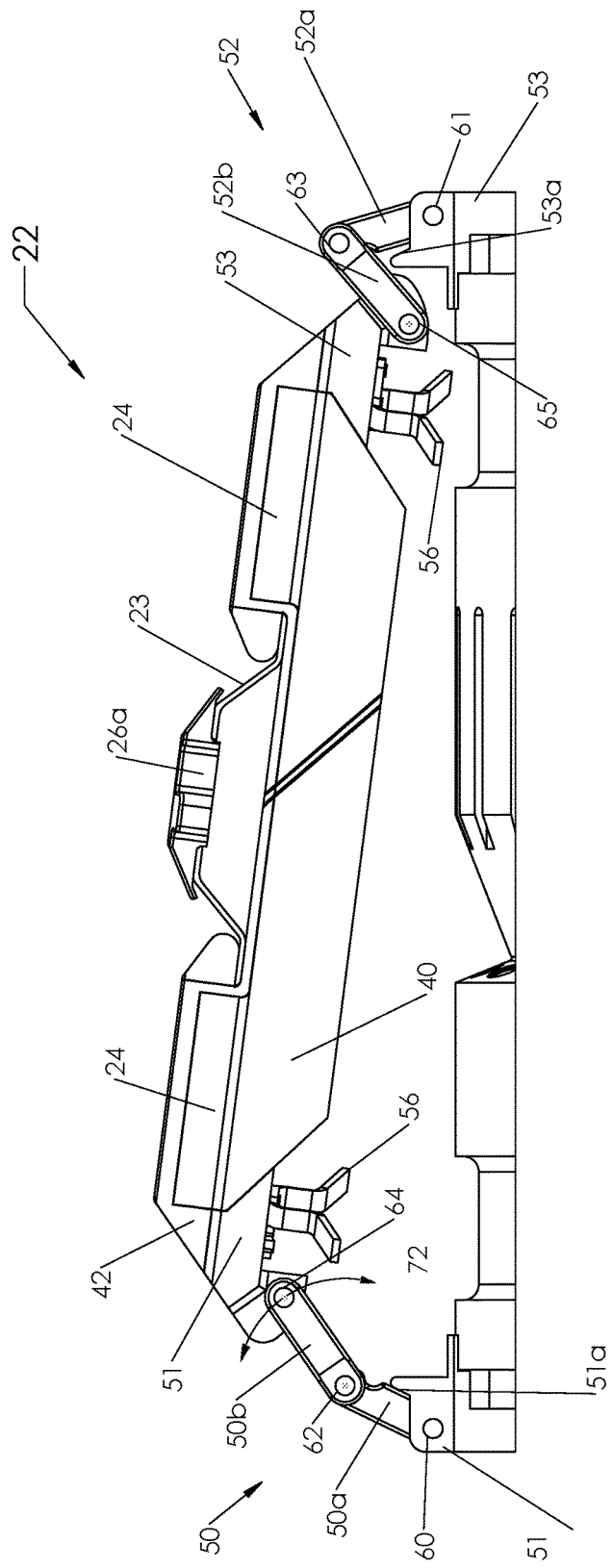
FIG. 10 is an elevation view of one embodiment of a collapsing inspection assembly attached to a section of an ILI tool as the ILI tool moves in a forward direction to the left in accordance with an embodiment of the present invention.

FIG. 10 illustrates action of the magnetic assembly 22 as its two degrees of freedom are both active. As the ILI tool 10 moves forward to the left, sub-linkage 50a comes into contact with the sloping or normal surface 51a of block 51 and is held in that position. Sub-linkage 50a is fixed relative to the central body of the ILI tool 10 and pivot 60 is not active. Sub-linkage 50b is free to rotate about pivot 62 and the magnetic assembly 22 may translate along the curvilinear path 72. Magnetic assembly 22 is constrained to movement in its radial plane by linkages 50 and 52 and those linkages control its movement within its radial plane. At the rear end of magnetic assembly 22, sub-linkages 52a and 52b are displaced away from the supporting structure of block 53 and they may rotate with respect to one another. They do not restrict movement of the back end of magnetic assembly 22 within the radial plane and the magnetic assembly may rotate about pivot 64 as pivot 64 and the front end of the magnetic assembly 22 translate along curvilinear path 72. Thus the magnetic assembly may both translate and rotate, allowing it to reach positions as illustrated in FIG. 10 or any similar position as may occur within its radial plane. Concurrent translation and rotation allow magnetic section 22 to rock as it passes over intrusions into the pipe interior, allowing it to pass features such as welds, dents, damaged pipe wall, mechanical joints and other local pipeline features while closely contacting the pipe interior without excessive liftoff.

Figure 11:
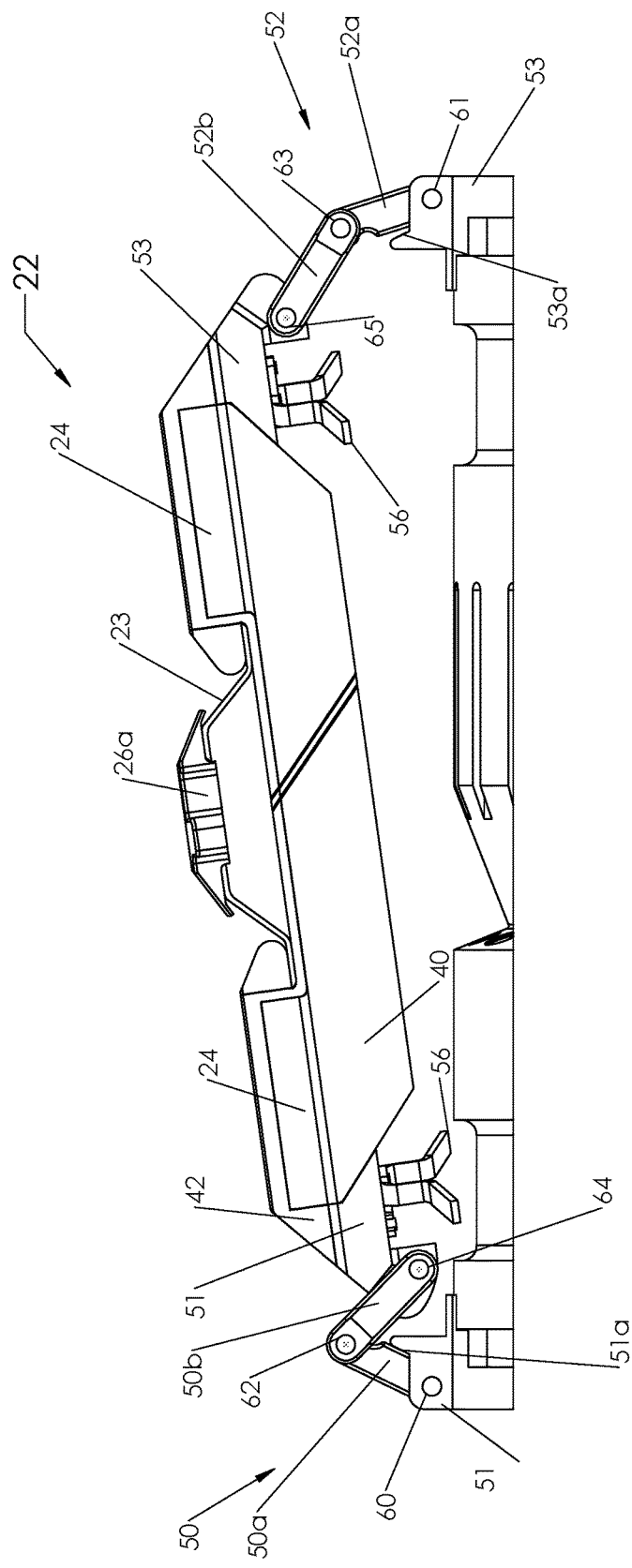
FIG. 11 is an elevation view of one embodiment of a collapsing inspection assembly attached to a section of an ILI tool as the ILI tool moves in a reverse direction to the right in accordance with an embodiment of the present invention.

Since sub-linkages 50b, 52a and 52b are free to move in their radial plane, magnetic assembly 22 may rotate clockwise as shown in FIG. 10 or counterclockwise as shown in FIG. 11. As they rotate in either direction, magnetic assemblies 22 are free to rock over any disturbances such as welds or dents on the interior surface of the pipeline.

Similarly, when the ILI tool 10 moves in a reverse direction, the magnetic assembly may also reach positions as illustrated in FIGS. 10 and 11. When reverse movement occurs, magnetic assemblies 22 are free to rock over any disturbances such as welds or dents on the interior surface of the pipeline.

FIGS. 5 through 11 illustrate typical movement of the magnetic assembly 22 positioned for various movement according to an embodiment of the invention. It is emphasized that these illustrations do not limit the applicability of the invention and that the invention applies to other inspection technologies as well as to other MFL configurations.

Figure 12:
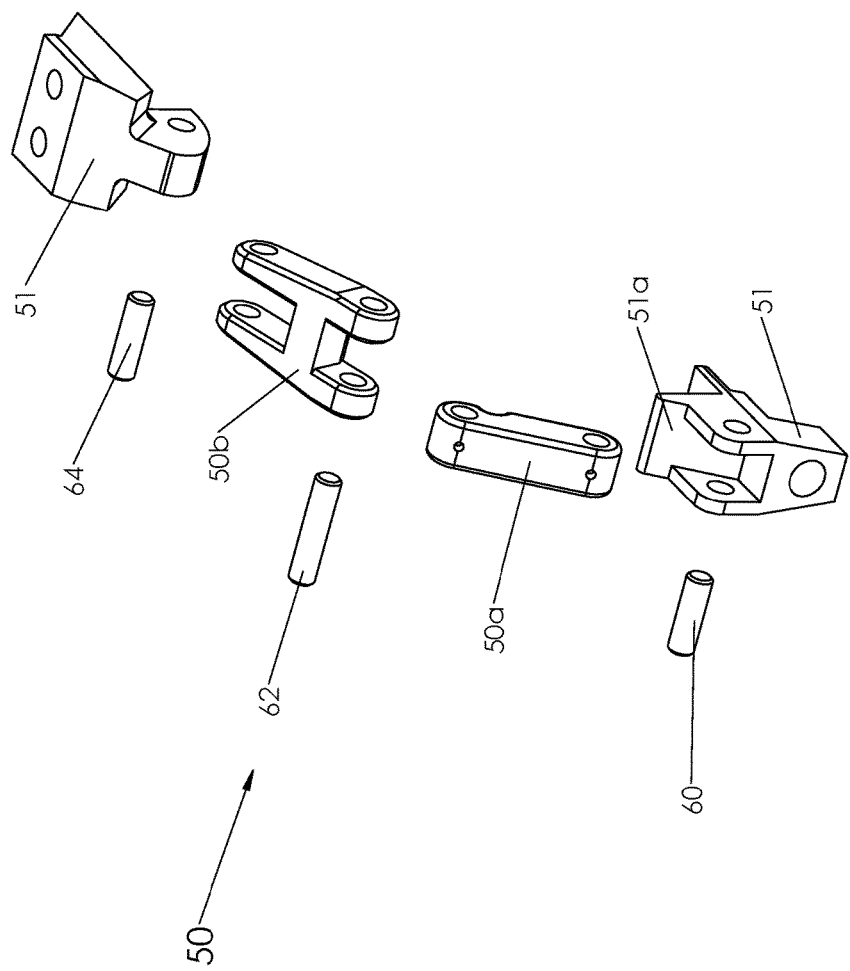
FIG. 12 is an exploded perspective view of one embodiment of linkage components of an ILI tool in accordance with an embodiment of the present invention as they may be positioned to limit their movement.
Figure 13:
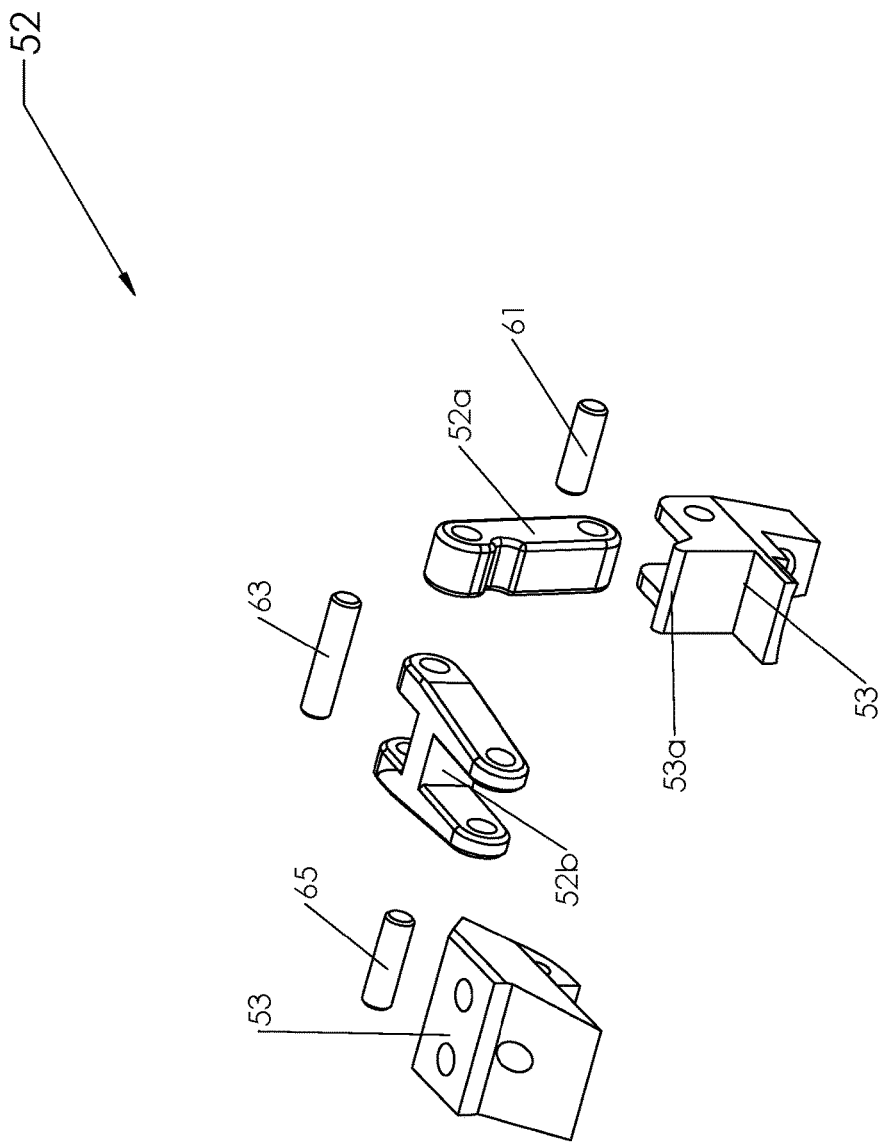
FIG. 13 is an exploded perspective view of one embodiment of linkage components of an ILI tool in accordance with an embodiment of the present invention as they may be positioned to free their movement.

FIG. 12 is an exploded view of Linkage 50 with its sub-linkages and mounting block as previously discussed. This figure discloses more detail and therefore better understanding of the unique features of the invention. As discussed in conjunction with FIG. 8, FIG. 12 shows sub-linkage 50a which may rest in contact with sloping or normal surface 51a on block 51 as the ILI tool 10 moves forward. When this contact is made and preserved by forward motion, sub-linkage 50a is effectively fixed to the central body of the ILI tool 10. Similarly, pivot 60 is not active and sub-linkage 50b may rotate about pivot 62 only. The free end of sub-linkage 50b may only rotate on a circular path about pivot 62 as shown by the curvilinear path 72 in FIG. 8. Sub-linkage 50b is then the only active linkage at the forward end of the magnetic assembly 22. Simultaneously, linkage 52 at the other end of magnetic assembly 22 is shown in the exploded view of FIG. 13. In FIG. 13, sub-linkage 52a does not contact its support block 53 while sub-linkage 50a is in contact with support block 51 as shown in FIGS. 8 and 12. Instead, sub-linkage 52a is free of block 53 and therefore it is free to rotate about pivot 61. Sub-linkage 52b is also free to rotate about moving pivot 63. While linkage 52 comprised of sub-linkages 52a and 52b (together with linkage 50) constrains the magnetic assembly 22 to movement within its radial plane, it provides no other constraint within the radial plane and the magnetic assembly 22 is free to move other than as it is constrained by pivot 64 at the other end of the assembly 22. There are thus two but only two degrees of freedom of magnetic assembly 22 within its radial plane.

When the ILI tool 10 moves in reverse, it is readily seen that sub-linkage 52a will become fixed in relation to the central body of the ILI tool 10, sub-linkage 50a will become free of constraint by the sloping or normal surface 51a of block 51 and that the process is fully analogous to that discussed above except that it occurs when movement of the ILI tool 10 is in reverse rather than forward. Magnetic assembly 22 may move with two degrees of freedom, one translation and one rotation, whether movement is forward or reverse. It should also be noted that the translation is along curvilinear path 72 at the front of magnetic assembly 22 as shown in FIG. 8 when the ILI tool 10 moves forward and along curvilinear path 73 at the rear of magnetic assembly 22 as shown in FIG. 9 when the ILI tool 10 moves in reverse. Movement of magnetic assembly 22 is controlled at the pivot pulling it in the direction of movement, and the pivot doing the pulling is always at the end of magnetic assembly 22 in the direction of movement.

Figure 14:
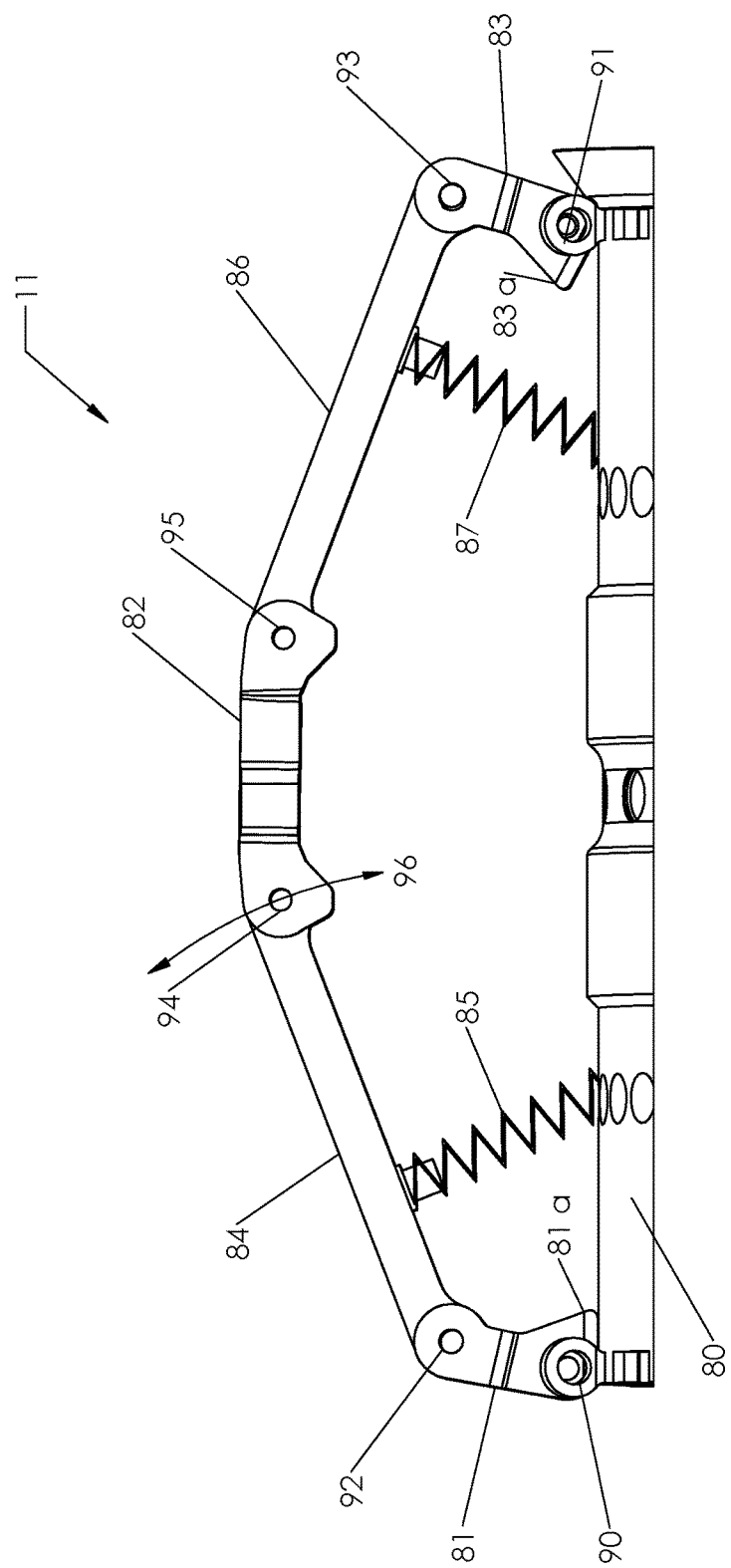
FIG. 14 is a sectional view of an embodiment of an inspection assembly in accordance with an embodiment of the present invention using technology other than MFL technology as it moves forward.

FIG. 14 shows a configuration of alternate inspection assemblies 11 with linkages according to an embodiment of the invention wherein stops on the linkages may control motion of the inspection assembly rather than blocks on the central portion of the ILI tool 10. This figure also shows an application to inspection technology other than MFL technology. Alternate inspection devices 82 may comprise technology such as ultrasonic inspection (UT), electromagnetic acoustic transducers (EMAT), eddy current, low field MFL, geometry or other technology. Linkages 81 and 83 may comprise extensions 81a and 83a that contact a fixed part of their supporting structure such as a canister 80 of the ILI tool 10. In the absence of magnetic force of attraction positioning an inspection device 82 at or near the pipe wall, supplemental support such as springs 85 and 87 or other mechanisms may provide such positioning. When the ILI tool 10 moves forward to the left, forces such as friction between inspection device 82 and the pipe wall or inertia rotate linkage 81 about pivot 90 until an extension 81a on the linkage contacts a stop. When that occurs, movement of linkage 81 relative to the support structure or central part of ILI tool 10 stops and linkage 81 is effectively fixed to the central part of ILI tool 10. Linkage 84 is then in tension and it pulls inspection device 82 forward to the left in the direction of movement of the ILI tool 10. Pivot 92 and the inner end of linkage 84 are effectively attached to the body of ILI tool 10. Pivot 94 and linkage 84 may only rotate about pivot 92. The forward end of inspection device 82 may only move in translation along the curvilinear path 96, which is the rotation of the outer end of linkage 84. Simultaneously, linkage 83 at the rear support pivot 91 rotates about pivot 91 and the support extension 83a moves away from its stop. Linkages 83 and 86 may rotate freely and the trailing end of inspection device 82 at pivot 95 may move in rotation about translating pivot 94 and the forward end of inspection device 82. Inspection device 82 then has two degrees of freedom, translation of its forward end along curvilinear path 96 and rotation about its rearward end. The movement is controlled by linkage 84 at the forward pivot 92.

Figure 15:
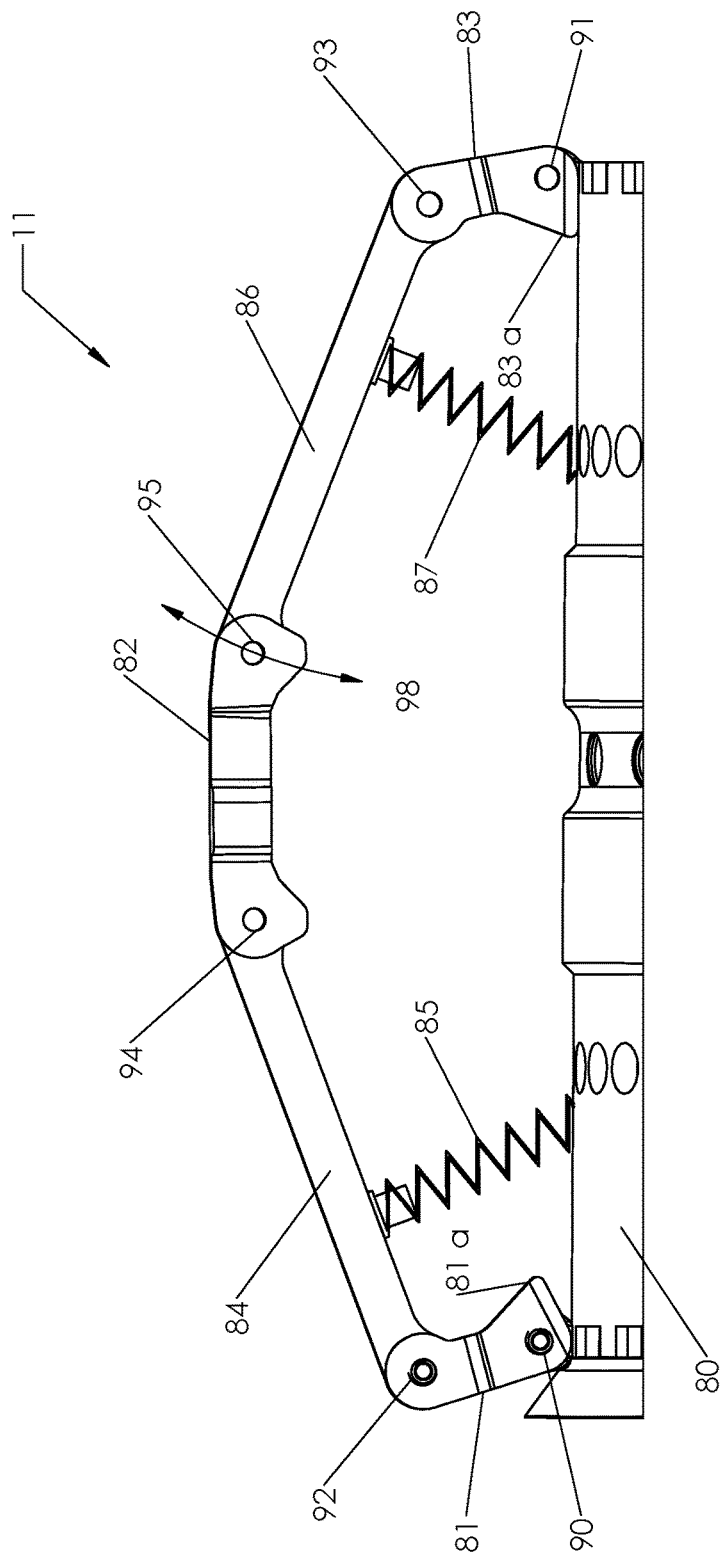
FIG. 15 is a sectional view of an embodiment of an inspection assembly in accordance with an embodiment of the present invention using technology other than MFL technology as it moves in reverse.

When an assembly such as that shown in FIG. 14 is subject to reverse movement of ILI tool 10, a full analogous movement of the assembly occurs as shown in FIG. 15.

Linkage 83 is rotated until its extension 83a contacts a stop. Linkage 83 is then in tension and pulls linkage 86, pivot 95 and inspection device 82 rearward toward the right. Pivot 95 and the rearward end of inspection device 82 move in translation along a curvilinear path 98, which is the rotation of the outer end of linkage 86. Simultaneously, linkage 81 moves away from its stop and pivot 94 together with the forward end of inspection device 82 may move in rotation about translating pivot 95 and the rearward end of inspection device 82. Inspection device 82 again has two degrees of freedom, translation of its rearward end along curvilinear path 98 and rotation about its forward end. Control of the movement has then shifted rearward and is controlled by linkage 86 at the rearward pivot 93.

The embodiment as illustrated in FIG. 1 further comprises drive mechanisms 20 that allow reverse motion to occur. One embodiment of the invention comprises special drive mechanisms with surfaces at their extreme diameter that seal against the pipe wall and conform to movement of the ILI tool 10 in either the forward or reverse direction. Another embodiment of the invention may comprise conventional disc drive mechanisms with a constant thickness (not shown but common in the fields of pipeline inspection or cleaning) that contact the pipe wall to seal against differential pressure across the mechanism that drives the ILI tool 10. A further embodiment of the invention may comprise conventional cup shaped drive mechanisms that allow the ILI tool to move in one direction only, either forward or reverse.

A sensor mount 23 as shown in FIGS. 2, 4 and 5 mounting sensors 26a to armature 40 may comprise flexible material. Accordingly, a sensor mount 23 may permit relative motion between a sensor 26a and an armature 40. Constraints such as wear plates 42 may be positioned proximate a sensor mount 23 to control or limit motion of the sensor mount 23 and sensor 26a with respect to the armature 40. In selected embodiments, a constraint 42 may prevent the sensor housing from contacting or being crushed by the armature 40. Accordingly, a constraint 42 may provide an additional control over the motion of a sensor 26a with respect to an armature 40.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A sensor system comprising:
a central body defining a central axis; and
a plurality of sensor assemblies mounted to the central body and distributed circumferentially around the central axis, each sensor assembly of the plurality of sensor assemblies including—
  a sensor body having at least one sensor mounted thereto; and
  first and second linkage assemblies mounted to the sensor body having the at least one sensor positioned between the first and second linkage assemblies, each linkage assembly of the first and second linkage assemblies including (a) a first link, (b) a second link, (c) a first pivot coupling the first link to the central body, (d) a second pivot coupling the second link to the first link, (e) a third pivot coupling the second link to the sensor body, and (f) a block positioned to prevent rotation of at least one of the first and second links about one of the first, second, and third pivots in response to urging of the sensor body away from the each linkage assembly.

2. The sensor system of claim 1, wherein the block is positioned to permit rotation of the at least one of the first and second links about the one of the first, second and third pivots in response to urging of the sensor body toward the each linkage assembly.

3. The sensor system of claim 2, wherein the block is positioned to restrict rotation of the first link about the first pivot in response to urging of the sensor body away from the each linkage assembly.

4. The sensor system of claim 3, wherein:
the central body defines a radial direction perpendicular to the central axis and radiating outward from the central axis;
the block is positioned to restrict rotation of the first link such that the second pivot is rotatable inwardly from the first pivot no more than 45 degrees from the radial direction.

5. The sensor system of claim 4, wherein the block is positioned to restrict rotation of the first link such that the second pivot is rotatable inwardly from the first pivot no more than 35 degrees from the radial direction.

6. The sensor system of claim 4, wherein the block is positioned to restrict rotation of the first link such that the second pivot is rotatable inwardly from the first pivot no more than 32 degrees from the radial direction.

7. The sensor system of claim 4, wherein the block is positioned to permit rotation of the first link outwardly from the first pivot by at least 60 degrees.

8. The sensor system of claim 3, wherein the block is mounted to the central body.

9. The sensor system of claim 8, wherein the first pivot rotatably secures the first link to the block.

10. The sensor system of claim 9, wherein the block defines a sloped surface facing outwardly and defining an angle of between 25 and 35 degrees with respect to the radial direction.

11. The sensor system of claim 1, wherein the block is secured to the first link.

12. The sensor system of claim 1, wherein the first and second linkage assemblies are sized and positioned relative to one another such that the first, second, and third pivots of the first and second linkage assemblies are not permitted to move such that an inward facing angle between the first and third pivots about the second pivot exceeds 180 degrees.

13. The sensor system of claim 1, wherein the at least one sensor is a magnetic flux leakage (MFL) sensor.

14. The sensor system of claim 1, wherein the at least one sensor is an ultrasonic sensor.

15. The sensor system of claim 1, wherein the at least one sensor is an electromagnetic acoustic transducer (EMAT).

16. The sensor system of claim 1, wherein the first, second, and third pivots permit rotation exclusively in a radial plane, the radial plane being parallel to the central axis and radiating outwardly from the central axis.

17. A method for inspecting a pipeline comprising:
providing a sensor system including (A) a central body defining a central axis and (B) a plurality of sensor assemblies mounted to the central body and distributed circumferentially around the central axis, each sensor assembly of the plurality of sensor assemblies including (i) a sensor body having at least one sensor mounted thereto and (ii) first and second linkage assemblies mounted to the sensor body having the at least one sensor positioned between the first and second linkage assemblies, each linkage assembly of the first and second linkage assemblies including (a) a first link, (b) a second link, (c) a first pivot coupling the first link to the central body, (d) a second pivot coupling the second link to the first link, and (e) a third pivot coupling the second link to the sensor body, (f) a block positioned to prevent rotation about one of the first, second, and third pivots in response to urging of the sensor body away from the each linkage assembly;
inserting the sensor system in the pipeline such that the sensor bodies of the plurality of sensor assemblies engage an inner wall of the pipeline;
urging the sensor system through the pipeline in a first direction such that the inner wall urges the sensor bodies of the plurality of sensor assemblies toward the first linkage assemblies thereby causing the blocks of the first linkage assemblies to prevent rotation about the one of the first, second and third pivots of the first linkage assemblies;
urging the sensor system through the pipeline in a second direction opposite to the first direction such that the inner wall urges the sensor bodies of the plurality of sensor assemblies away from the first linkage assemblies thereby causing the blocks of the first linkage assemblies to cease preventing rotation about the one of the first, second and third pivots of the first linkage assemblies.

18. The method of claim 17, wherein causing the blocks of the first linkage assemblies to prevent rotation about one of the first, second, and third pivots of the first linkage assemblies comprises urging the first link into engagement with the block.

19. The method of claim 18, wherein causing the blocks of the first linkage assemblies to cease preventing rotation about the one of the first, second and third pivots of the first linkage assemblies comprises urging the first link out of engagement with the block.

* * * * *